United States Patent [19]
Julius et al.

[11] Patent Number: 6,011,157
[45] Date of Patent: Jan. 4, 2000

[54] PROCESS FOR PURIFYING STERICALLY HINDERED 4-AMINO PIPERIDINES

[75] Inventors: Manfred Julius, Limburgerhof; Harald Rust, Neustadt; Alfred Krause; Hardo Siegel, both of Speyer; Wolfgang Siegel, Limburgerhof; Tom Witzel, Ludwigshafen, all of Germany

[73] Assignee: BASF Aktiengesellschaft, Ludwigshafen, Germany

[21] Appl. No.: 09/180,626

[22] PCT Filed: May 30, 1997

[86] PCT No.: PCT/EP97/02822

§ 371 Date: Nov. 12, 1998

§ 102(e) Date: Nov. 12, 1998

[87] PCT Pub. No.: WO97/46529

PCT Pub. Date: Dec. 11, 1997

[30] Foreign Application Priority Data

Jun. 3, 1996 [DE] Germany .................. 196 22 269

[51] Int. Cl.[7] .................. C07D 211/58; C07D 221/20
[52] U.S. Cl. .................. 546/244; 546/187
[58] Field of Search .................. 546/244, 187; 564/477, 503

[56] References Cited

U.S. PATENT DOCUMENTS

| | | | |
|---|---|---|---|
| 3,159,276 | 12/1964 | Moore | 564/477 |
| 3,222,310 | 12/1965 | Hinckley . | |
| 3,922,306 | 11/1975 | Takaku et al. | 564/477 |
| 5,208,377 | 5/1993 | Overgaard et al. | 564/477 |

FOREIGN PATENT DOCUMENTS

| | | |
|---|---|---|
| 33 529 | 8/1981 | European Pat. Off. . |
| 477 593 | 1/1995 | European Pat. Off. . |
| 266 799 | 4/1989 | Netherlands . |
| 1811527 | 4/1993 | U.S.S.R. . |

OTHER PUBLICATIONS

Ohtawara et al. "Method of manufacturing acylated amines and slats and quaternary ammonium saltsthereof as fabric softeners" CA 130:209434, 1997.

Speciality Chem. 4 (2), pp. 38, 40, 41 (1984).

*Primary Examiner*—Ceila Chang
*Attorney, Agent, or Firm*—Keil & Weinkauf

[57] ABSTRACT

A process for purifying crude piperidines of the formula I

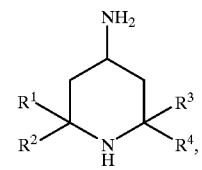

I where $R^1$ to $R^4$ are $C_1$–$C_6$-alkyl, or $R^1$ and $R^2$ and/or $R^3$ and $R^4$ together are a $CH_2$-chain of 2 to 5 carbons, which comprises, in a first step, removing high-boiling substances and, if present, water from the crude piperidines by distillation; in a second step, adding from 0.01 to 5% by weight, based on the product of the first step, as a reducing agent; and, in a third step, isolating the piperidines by distillation.

4 Claims, No Drawings

PROCESS FOR PURIFYING STERICALLY HINDERED 4-AMINO PIPERIDINES

This application is a 371 of PCT/EP97/02822 filed May 30, 1997

The invention relates to a process for purifying crude piperidines of the formula I

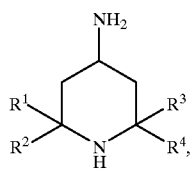

where $R^1$ to $R^4$ are $C_1$–$C_6$-alkyl or $R^1$ and $R^2$ and/or $R^3$ and $R^4$ together are a $CH_2$-chain of 2 to 5 carbons.

Sterically hindered 4-aminopiperidines of the formula I are widely employed. They are used in particular as intermediates in the preparation of UV stabilizers for synthetic polymers. It is therefore of great importance that the piperidines I possess as little inherent coloration as possible and retain this quality over a long period despite even the slightest content of by-product.

The industrial preparation of the sterically hindered 4-aminopiperidines generally starts from acetone or acetone derivatives. Compounds I can be obtained in one stage, in a catalytic ring closure reaction in the presence of ammonia and hydrogen, from the compounds

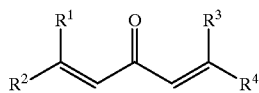

(DE 2 412 750), or from triacetoneamines II

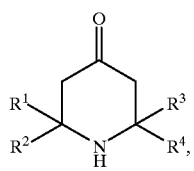

by aminative hydrogenation in one or two stages, for example under catalysis (see for example DE 2 040 975, DE 2 349 962, DE 26 21 870, EP 33 529, EP 42 119, EP 303 279, EP 410 970, EP 611 137, EP 623 585 and DE 42 10 311). These industrially prepared sterically hindered 4-aminopiperidines are generally purified by distillation.

However, the piperidines I prepared by customary techniques usually still contain disruptive amounts of coloring substances, or else such substances are formed after a short time.

Against the background of this state of affairs it was known, for example from EP 477 593, that crude N-alkyldialkanolamines can be improved in terms of color by adding a metal borohydride and carrying out distillation in the presence of water under defined conditions. However, the N-alkyldialkanolamines are a totally different class of substance from the sterically hindered 4-aminopiperidines of the present invention. Furthermore, it was known from Spec. Chem. 4(2), (1984) 38–41 and from U.S. Pat. No. 3,159,276, U.S. Pat. No. 3,207,790 and U.S. Pat. No. 3,222,310 that it is possible to improve the color of the products by adding sodium borohydride to ethanolamines, ethyleneamines or aromatic amines before or after distillation. This document too makes no mention of the piperidines I. No particular distillation technique is suggested.

In contrast, the development of methods for high purification of the sterically hindered 4-aminopiperidines took a very different path.

From DD 266 799 it was known to react piperidines I in solution in acetone/water with $CO_2$, to separate off the precipitate and wash it with acetone, and then to subject it to thermal decomposition and to purify the product by distillation. SU 18 11 527 describes another purification technique for sterically hindered 4-aminopiperidine I: the contaminated, crude product is dissolved in an aprotic solvent and reacted with ethylene glycol, and the reaction product is distilled and purified over a number of steps. Both techniques are extremely laborious and costly.

It is an object of the present invention, therefore, to provide a cost-effective process by which highly pure color-stable sterically hindered 4-aminopiperidines I can be made available, ie. products whose low degree of inherent coloration is retained over long periods and coupled with a low content of by-products, such as stabilizing auxiliaries.

We have found that this object is achieved by the above-mentioned process, which comprises, in a first step, removing high-boiling substances and, if present, water from the crude piperidines by distillation; in a second step, adding from 0.01 to 5% by weight, based on the product of the first step, of a reducing agent; and, in a third step, isolating the piperidines by distillation.

Other features of the invention are evident from the subclaims.

In the sterically hindered 4-aminopiperidines I, $R^1$, $R^2$, $R^3$ and $R^4$ independently are preferably $C_1$–$C_3$-alkyl, especially ethyl or methyl, for example methyl.

The reducing agents used are generally substances which are solid under standard conditions, advantageously compounds $MXH_{4-m}Y_m$, in which M is an alkali metal, $NR_4$, where each R is an identical or different $C_1$–$C_4$-alkyl, or one equivalent of an alkaline earth metal or one equivalent of zinc, preferably an alkali metal, especially sodium or potassium, for example sodium, X is aluminum or, in particular, boron, Y is CN or, preferably, H, and m is 1 or, in particular, 0. An example is sodium borohydride. In some cases $(R^aO)_2TiBH_4$ or $(R^aO)_3TiBH_4$, where $R^a$ is $C_1$–$C_4$-alkyl, has been found suitable.

The novel process can be carried out continuously or batchwise and at atmospheric or, preferably, under reduced pressure, in particular at from 10 to 200 mbar, for example from 20 to 100 mbar.

Unless stated otherwise, the boiling points or boiling ranges specified relate to a pressure of 40 mbar. They refer in each case to the purification of 4-amino-2,2,6,6-tetramethyl-piperidine. For other 4-aminopiperidines I the skilled worker can derive the appropriate conditions by means of simple experiments.

The term high-boiling substances refers in general to those substances having a boiling point of at least 35° C. above that of the desired product under a pressure of 40 mbar. In the case of 4-amino-2,2,6,6-tetramethylpiperidine, the high-boiling substances are removed by distillation, for example, at 140° C. under 40 mbar.

In the first step, the crude product is freed by distillation from high boilers and, in a particular embodiment of the invention, from water. This is generally done by (a) rectification, in which the high boilers are removed as liquid phase and the water from the top in one step, or (b) alternatively, by distilling off the crude product from the high boilers in appropriate apparatus, such as wiper blade evaporators, falling film evaporators or stirred vessels with a condenser attachment, followed by distillative removal of the water. The separation of water is not critical and can be carried out, for example, at 100 mbar and at from 40 and 50° C., or appropriately at different pressures. To separate off the high boilers, the liquid phase in the distillation is generally heated at up to 140° C. (under 40 mbar). The smaller the amount of the high boilers in the piperidine I, the better the results obtained. In general, contents of high-boiling components of below 0.1% by weight in the piperidine I can still be tolerated. However, contents of high boilers of less than 0.01% by weight are better. The water content is not critical and is normally adjusted to below 1% by weight.

Subsequently, in a second step, the reducing agent is added. An amount of from 0.01 to 2% by weight is generally sufficient to obtain a colorless product having the desired properties. Preference is given to the use of from 0.01 to 1% by weight, in particular from 0.01 to 0.5% by weight. The method of addition is not critical; the reducing agent is usually supplied to the liquid phase of the distillation and can be added in powder form or as a solution.

After the reducing agent has been added, the product is purified by distillation. This is normally done in known rectification columns, such as plate columns or packed columns, preferably the latter. Various reflux ratios can be operated, which the skilled worker can readily determine by means of brief preliminary experiments. A ratio which has proven suitable of reflux to the amount of product taken off is one of from 1:1 to 10:1, in particular from 3:1 to 7:1. The product 4-amino-2,2,6,6-tetra-methylpiperidine boils at 101° C. under 40 mbar, as the skilled worker is easily able to find out (see for example J. Polym. Sci., Part A-1, 10(11), (1972) 3295–310); consequently, it is normally obtained at from 96 to 103° C. (under 40 mbar).

To the product thus obtained, which is colorless per se, it is additionally possible to add small amounts of reducing agent in order to increase the stability on storage. Amounts of up to 200 ppm of reducing agent are normally sufficient. In particular cases 100, 50 or 10 ppm will be sufficient.

The novel process provides, in a simple and cost-effective manner, pure, sterically hindered 4-aminopiperidines I which have virtually no inherent coloration and which, on storage, remain stable in terms of color while at the same time having a very low content of by-products such as stabilizers.

EXAMPLES

The color of the sterically hindered 4-aminopiperidines I was determined by measuring the APHA-color number in accordance with DIN-ISO 6271.

Example 1

Crude 4-amino-2,2,6,6-tetramethylpiperidine (TAD) having the composition

| |
|---|
| 83.6% triacetonediamine (TAD) |
| 10.0% $H_2O$ |
| 1.5% low boilers |
| 4.9% middle and high boilers | was distilled in a wiper-blade evaporator (200 cm$^2$ evaporator surface, 400 rpm) at 140° C. under 40 mbar. With a feed rate of 500 g/h (preheated to 100° C.), a liquid-phase temperature of 106° C. and a column-head temperature of 89° C., 2560 g (92.3%) were distilled off. The composition of the distillate was as follows:

| |
|---|
| 87.2% triacetonediamine (TAD) |
| 9.9% $H_2O$ |
| 1.5% low boilers |
| 1.4% middle boilers. |

The crude TAD product freed in this way from high boilers was subsequently rectified in a column with a 2.4 m Sulzer-CY packing (about 22 theoretical plates, nominal width: 43 mm) at a reflux ratio of 5:1 under a pressure of 100 mbar. 256 g of water were distilled off first of all at a column-head temperature of from 43 to 44° C. In the still, 0.1% sodium borohydride was added to the liquid phase and the rectification was continued at 40 mbar. After separating off a fraction containing 85.9% of TAD (11 g), at a column-head temperature of 89° C., and a further fraction at a column-head temperature of 99° C., containing 98.4% of TAD (240 g), the main fraction resulting from the rectification, at a column-head temperature of from 99 to 102° C., comprises 1786 g of TAD with a purity of 99.8% (GC). This corresponds to a distillation yield of 77%.

A) Over a period of at least 5 weeks, this pure TAD material was found to be stable in color (APHA-color number <50), as shown by the table below.

B) A sample of the TAD obtained by this technique was also stored with the addition of 110 ppm of sodium borohydride. By means of this addition, a TAD product which was virtually uncolored for at least 5 weeks and, in addition, was color-stable, with an APHA color number of <15, was obtained.

The samples (A) and (B) were stored under identical conditions at room temperature.

| Storage | Color number (undiluted product) | |
|---|---|---|
| time in days | (A) no added $NaBH_4$— | (B) 110 ppm of $NaBH_4$ added |
| 13 | 43 | 5 |
| 14 | 37 | 6 |
| 16 | 37 | 5 |
| 18 | 38 | 4 |
| 19 | 40 | 3 |
| 20 | 38 | 7 |
| 21 | 41 | 11 |
| 22 | 36 | 8 |
| 25 | 48 | 13 |
| 32 | 36 | 3 |
| 39 | 43 | 4 |

Comparison Example 1

2987 g of crude TAD with the composition

| |
|---|
| 86.2% triacetonediamine (TAD) |
| 8.7% $H_2O$ |
| about 1.1% low boilers |
| 4.0% middle and high boilers | were rectified in a laboratory column with 2.4 m Sulzer-CY packing (about 22 theoretical plates, nominal width: 43 mm) at a reflux ratio of 5:1. Under a pressure of 100 mbar, an initial fraction of 349 g, containing predominantly water, was distilled off at from 43 to 44° C. Then 3.0 g (0.1% by weight) of sodium borohydride were added to the liquid phase of the distillation, which contained less than 0.1% of water, and the rectification was continued. After an initial fraction of 222 g of TAD with a purity of 99.0%, a main fraction was obtained at a pressure of 40 mbar, and a column-head temperature of 97° C. which comprised 2116 g of TAD with a purity of 99.7% (GC) and a water content of <0.1%; distillation yield: 2116 g (82%).

Despite storage under nitrogen in the dark for two days, the resulting pure TAD product underwent yellow discoloration (APHA color number >100).

Comparison Example 2

4208 g of crude TAD of the composition

| | |
|---|---|
| 85.6% | triacetonediamine (TAD) |
| 9.0% | H$_2$O |
| about 0.7% | low boilers |
| 4.7% | middle and high boilers | were rectified in a laboratory column with 2.4 m Sulzer-CY packing (about 22 theoretical plates, nominal width: 43 mm) at a reflux ratio of 5:1 under a pressure of from 100 to 40 mbar. Following the separation of the water in the initial fraction at from 43 to 44° C. under a pressure of 100 mbar, a main fraction was obtained under a pressure of 40 mbar and at a column-head temperature of from 97 to 103° C. which constituted a pure TAD fraction with a TAD content of >99.6% (GC); Distillation yield: 3022 g (84%).

A pure fraction (TAD content, according to GC: 99.7%) was stored in one case without sodium borohydride and in the other case after addition of various amounts of sodium borohydride, as in Example 1, and was measured. The result is shown by the following table:

| Storage time in | Color number (undiluted product): (in acc. with DIN-ISO 6271) | | |
|---|---|---|---|
| days | no NaBH$_4$ added | 1000 ppm | 100 ppm |
| 1 | 238 | 207 | 225 |
| 3 | 297 | 16 | 61 |
| 4 | 289 | 12 | 35 |
| 5 | 287 | 10 | 27 |
| 6 | 286 | 9 | 32 |
| 10 | 299 | 5 | 73 |
| 11 | 297 | 4 | 72 |
| 42 | 309 | 3 | 255 |

Although subsequent addition of large amounts of reducing agent (0.1% = 1000 ppm) does increase the color stability, it also produces an undesirable increase in the proportion of auxiliaries.

We claim:

1. A process for purifying crude piperidines of the formula I

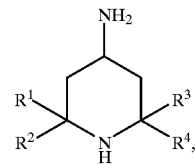

where R$^1$ to R$^4$ are C$_1$–C$_6$-alkyl, or R$^1$ and R$^2$ and/or R$^3$ and R$^4$ together are a CH$_2$-chain of 2 to 5 carbons, which comprises, in a first step, removing high-boiling substances and, if present, water from the crude piperidines by distillation; in a second step, adding from 0.01 to 5% by weight, based on the product of the first step, of a reducing agent; and, in a third step, isolating the piperidines by distillation.

2. A process as claimed in claim 1, wherein R$^1$, R$^2$, R$^3$ and R$^4$ are C$_1$–C$_3$-alkyl.

3. A process as claimed in claim 1, wherein the reducing agent is a compound of the formula MXH$_{4-m}$Y$_m$ where M is an alkali metal, NR$_4$, where each R is an identical or different C$_1$–C$_4$-alkyl, or one equivalent of an alkaline earth metal or one equivalent of zinc, X is boron or aluminum, Y is H or CN, and m is 0 or 1.

4. A process as claimed in claim 1, wherein from 0.001 to 0.02% by weight, based on the piperidines, of a reducing agent is added to the piperidines I isolated by distillation in the third step.

* * * * *